United States Patent
Rosenbaum et al.

(10) Patent No.: US 10,863,975 B2
(45) Date of Patent: Dec. 15, 2020

(54) ADJUSTABLE LENGTH, REUSABLE RETRACTION BLADES

(71) Applicant: CareFusion 2200, Inc., San Diego, CA (US)

(72) Inventors: Joanna Rosenbaum, Evanston, IL (US); Sara Tillman, Vernon Hills, IL (US); Andrew VanDeWeghe, Grayslake, IL (US); Timothy Hussey, Chicago, IL (US); Brandon Toth, Vernon Hills, IL (US); Bradley Williams, Round Lake Beach, IL (US); Jessica McQuaide, Vernon Hills, IL (US); Jason Cartwright, Libertyville, IL (US); Adam Fedenia, Libertyville, IL (US); Thomas Wilschke, Chicago, IL (US)

(73) Assignee: CareFusion 2200, Inc., San Diego, CA (US)

( * ) Notice: Subject to any disclaimer, the term of this patent is extended or adjusted under 35 U.S.C. 154(b) by 140 days.

(21) Appl. No.: 15/650,496

(22) Filed: Jul. 14, 2017

(65) Prior Publication Data
US 2019/0015089 A1 Jan. 17, 2019

(51) Int. Cl.
*A61B 17/02* (2006.01)
*A61B 17/00* (2006.01)

(52) U.S. Cl.
CPC ........ *A61B 17/0206* (2013.01); *A61B 17/025* (2013.01); *A61B 17/02* (2013.01); *A61B 2017/00991* (2013.01); *A61B 2017/0256* (2013.01)

(58) Field of Classification Search
CPC .... A61B 17/02; A61B 17/0206; A61B 17/025
See application file for complete search history.

(56) References Cited

U.S. PATENT DOCUMENTS

| 2,474,857 | A | | 7/1949 | Newman |
| 3,710,783 | A | * | 1/1973 | Jascalevich ............ A61B 17/02 600/228 |
| 5,782,753 | A | * | 7/1998 | DeFonzo ......... A61B 17/00008 600/201 |
| 5,928,139 | A | | 7/1999 | Koros et al. |
| 6,139,493 | A | | 10/2000 | Koros et al. |
| 8,758,235 | B2 | | 6/2014 | Jaworek |
| 8,932,210 | B2 | | 1/2015 | Woods |

(Continued)

*Primary Examiner* — Christopher J Beccia
(74) *Attorney, Agent, or Firm* — Dinsmore & Shohl LLP

(57) ABSTRACT

An adjustable retractor blade and retractor system are disclosed. The retractor blade includes a fixed portion, extendible portion, and means for adjusting the length of the retractor blade. The means for adjusting may include a threaded rod engaging the fixed portion with the extendible portion. In one aspect, the extendible portion includes a plurality of stackable members, with the length of the adjustable blade adjusted by attaching stackable members. In one aspect, the fixed portion includes a plurality of holes, and the extendible portion includes at least one post, the plurality of holes configured to receive the at least one post, with the length of the adjustable blade adjusted by slidably displacing the extendible portion until the at least one post engages with at least one of the plurality of holes. Methods are provided for adjusting the length of a retractor blade.

20 Claims, 9 Drawing Sheets

(56) References Cited

U.S. PATENT DOCUMENTS

| | | |
|---|---|---|
| 2008/0300465 A1 | 12/2008 | Feigenwinter et al. |
| 2009/0076516 A1 | 3/2009 | Lowry et al. |
| 2011/0034777 A1 | 2/2011 | Ames et al. |
| 2012/0116460 A1 | 5/2012 | Gorek |
| 2012/0271120 A1 | 10/2012 | Seex |
| 2013/0158359 A1 | 6/2013 | Predick et al. |
| 2014/0330086 A1* | 11/2014 | Mire .............. A61B 17/0218 600/215 |

* cited by examiner

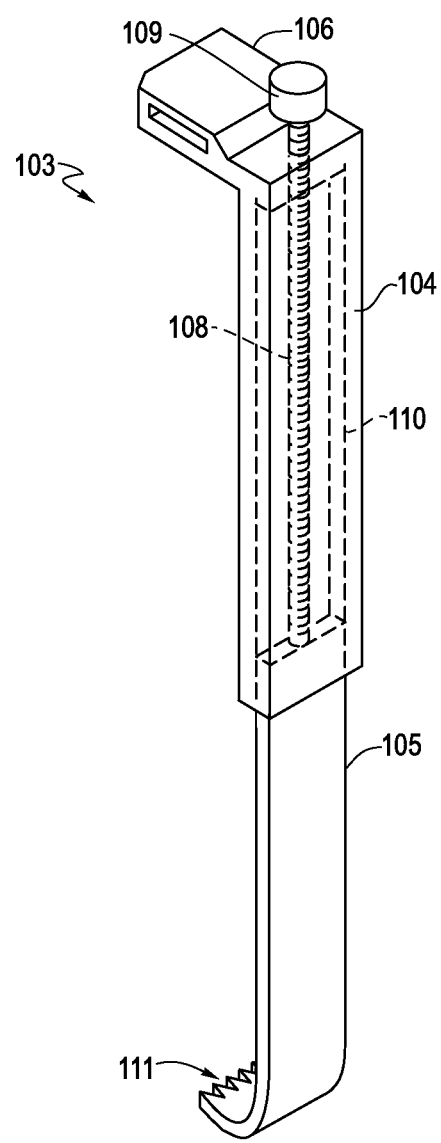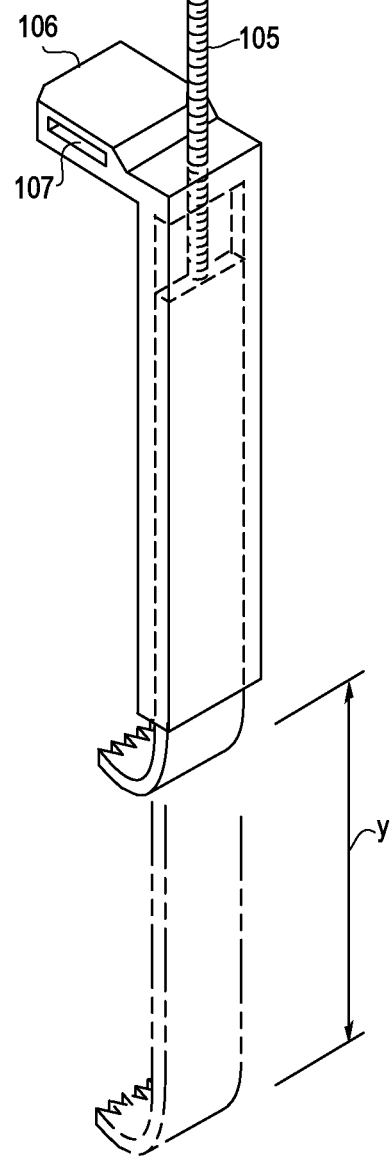

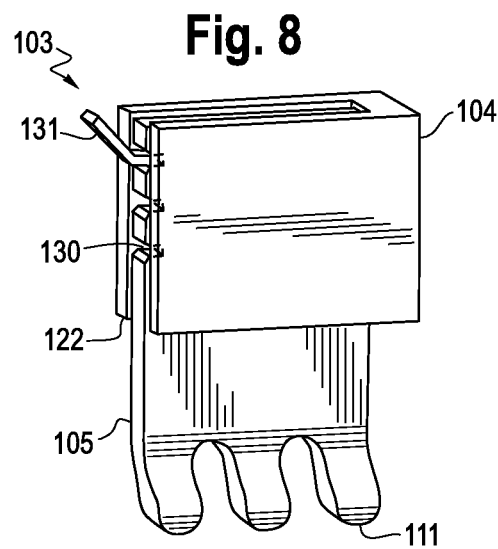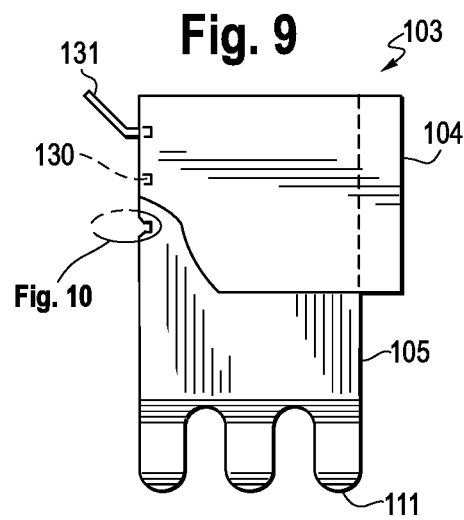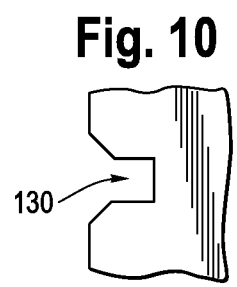

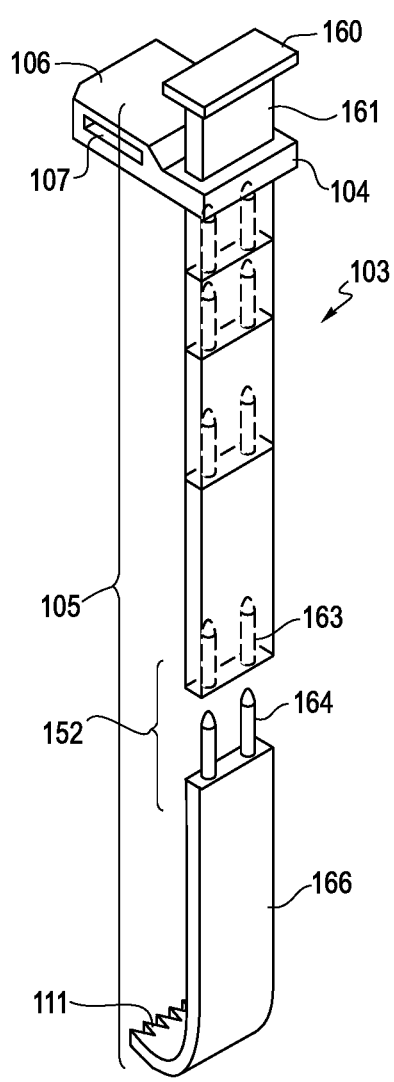
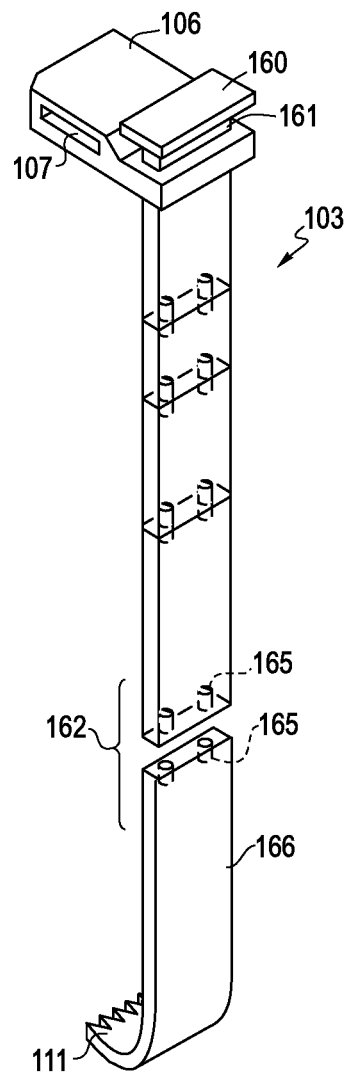

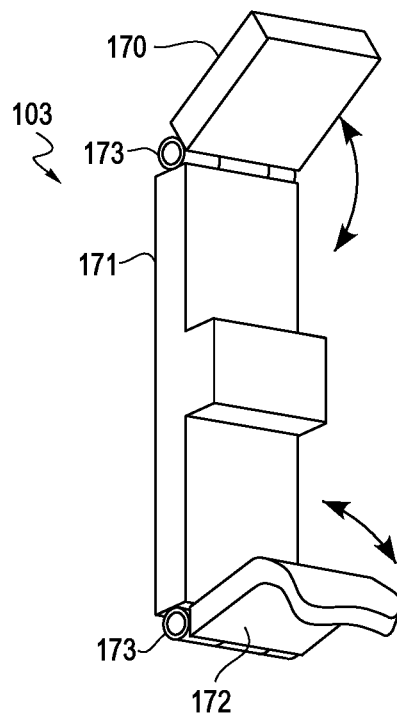
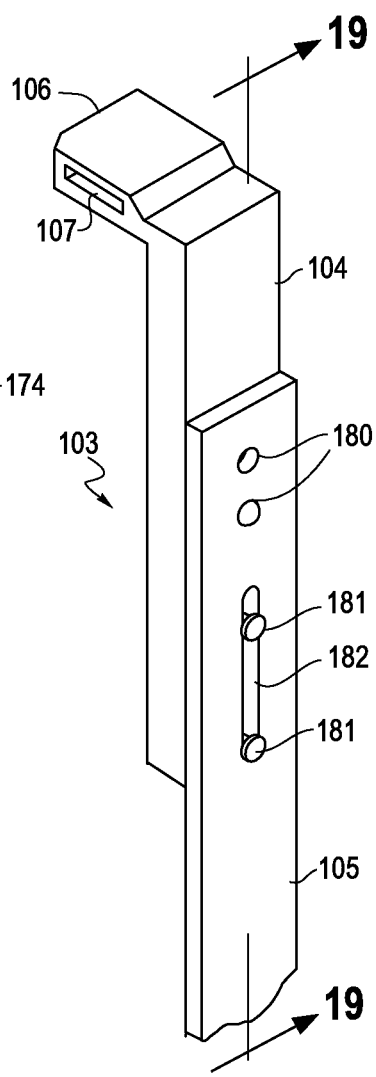
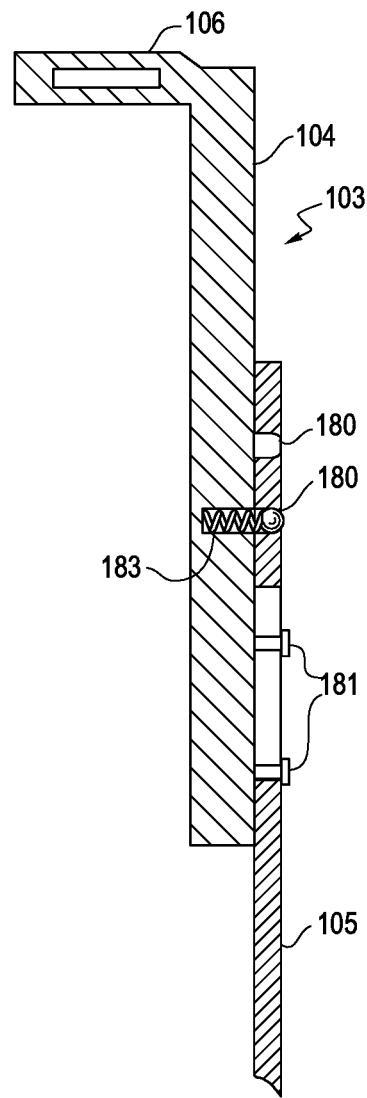

ADJUSTABLE LENGTH, REUSABLE RETRACTION BLADES

TECHNICAL FIELD

The disclosure generally relates to retractor systems used in surgery. More specifically, the disclosure relates to retractor blades that can be adjusted in length and methods of using the retractor blades.

BACKGROUND

Retractors and retractor frames are used to separate the edges of a surgical incision during various surgical procedures. Retractor blades allow practitioners to stably hold back surrounding tissues, facilitating easier access to a desired body part. For example, retractor blades may be used to separate soft tissue and expose vertebrae during spinal surgery.

Because of the significant variation in patient anatomy and surgeon preference, large sets of retractor blades of a variety of fixed lengths are normally prepared for each surgery, even though only a few of the blades may actually be used in a given procedure. Each of these fixed length retractor blades are generally made from a single piece of metal, which must be sterilized between procedures. This places a significant burden on staff, increases sterilization and equipment costs, and wastes clinical resources.

Adjustable-length retractor blades have been generally described, for example, in U.S. Pat. Nos. 2,474,857 and 5,928,139. These references describe extendible blades that slide longitudinally in channels on a fixed blade that is secured to a ratcheted retractor arm, with the extendible blade secured to the fixed blade using friction or spring-biased tensioners. These systems are not easily manipulated by a practitioner and have not gained widespread use. Accordingly, most clinicians continue to rely on large sets of fixed-length retractor blades.

It would be beneficial to provide an adjustable-length retractor blade that is easily manipulated to suit varying user needs and preferences, while addressing some of these limitations.

BRIEF SUMMARY OF SOME EXAMPLE EMBODIMENTS

In one aspect, an adjustable blade for surgical retraction is provided.

In embodiments, the adjustable blade includes a fixed portion, an extendible portion, and means for adjusting the length of the adjustable blade. In some embodiments, the fixed portion includes a proximal end, a distal end, and one or more channels. In some embodiments, the extendible portion is engaged with the one or more channels and longitudinally displaceable therein. In some embodiments, the means for adjusting the length of the retractor blade is a threaded rod or screw. Additional means for adjusting the length of the retractor blade are further provided.

In embodiments, the adjustable blade includes a fixed portion; an extendible portion having a plurality of stackable members; and means for reversibly attaching the plurality of stackable members to each other. In some embodiments, the length of the adjustable blade is adjusted by attaching or detaching members of a plurality of stackable portions on the extendible portion.

In embodiments, the adjustable blade includes a fixed portion having at least one depressable post near its distal end; an extendible portion having one or more channels configured to engage the fixed portion, and a plurality of holes configured to receive the at least one depressable post. In certain embodiments, the length of the adjustable blade is adjusted by slidably displacing the extendible portion until the at least one depressable post engages with at least one of the plurality of holes at a desired length.

In one aspect, methods are disclosed for adjusting a retractor blade.

BRIEF DESCRIPTION OF THE DRAWINGS

FIG. 2 illustrates a perspective view of an extended adjustable retractor blade, according to certain embodiments herein.

FIG. 3 illustrates a perspective view of a contracted adjustable retractor blade, according to certain embodiments herein.

FIG. 8 illustrates a perspective view of an adjustable retractor blade, according to certain embodiments herein.

FIG. 9 illustrates a frontal view of an adjustable retractor blade, according to certain embodiments herein.

FIG. 10 illustrates a detail of the locking mechanism for the adjustable retractor blade of FIGS. 8-9, according to certain embodiments herein.

FIGS. 15 and 16 illustrate perspective views of an adjustable retractor blade, according to certain embodiments herein.

FIG. 17 illustrates a perspective view of an adjustable retractor blade, according to certain embodiments herein.

FIG. 18 illustrates a perspective view of an adjustable retractor blade, according to certain embodiments herein.

FIG. 19 illustrates a side view of the adjustable retractor blade of FIG. 18 emphasizing a possible locking mechanism, according to certain embodiments herein.

DETAILED DESCRIPTION

Figure 1:
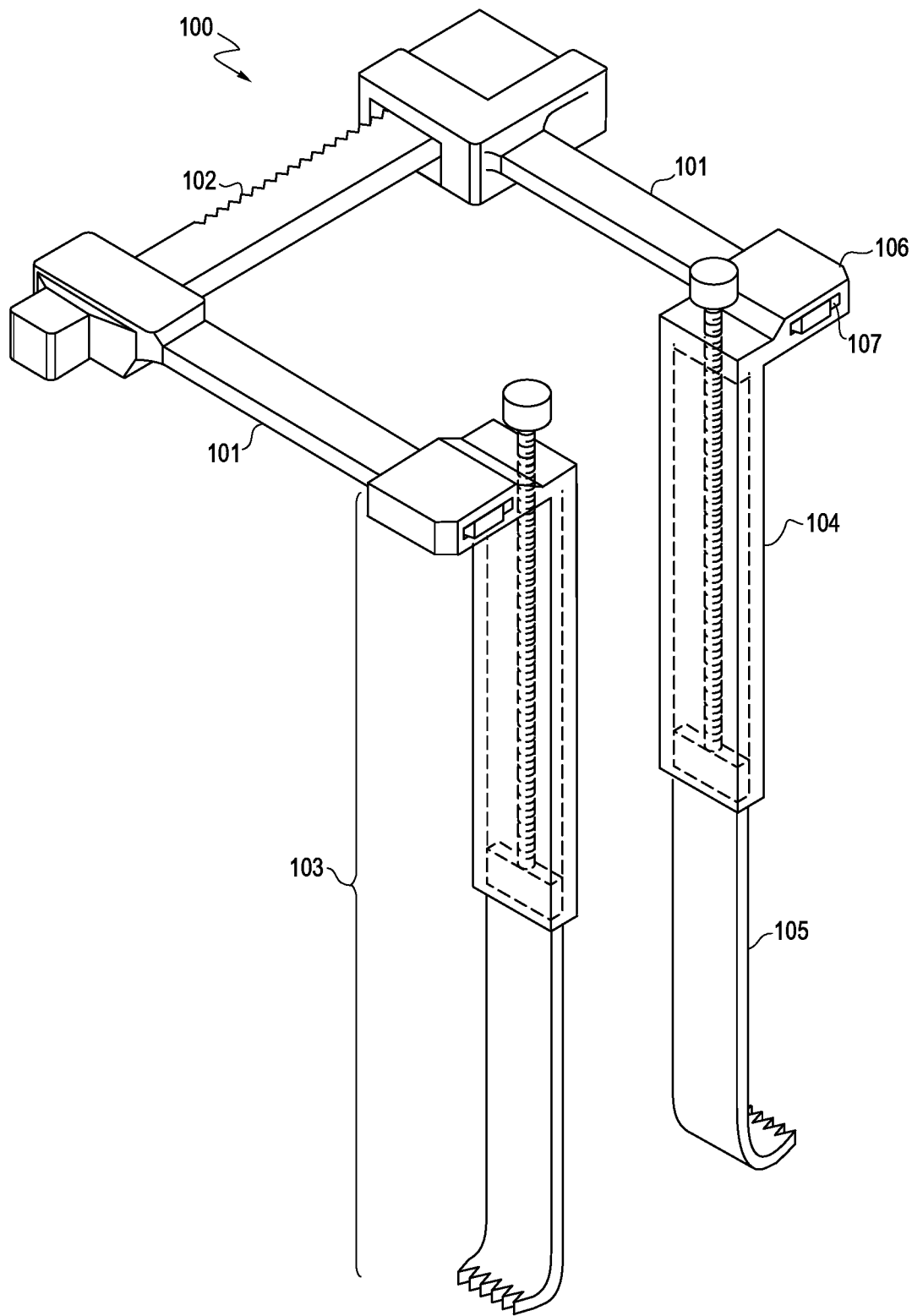
FIG. 1 illustrates a surgical retractor system including a pair of adjustable retractor blades, retractor arms, and retractor mount.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein such as, for example, conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry standards (e.g., ASTM, ANSI, IEEE standards) is defined as complying with the currently published standards as of the original filing date of this disclosure concerning the units, measurements, and testing criteria communicated by those standards unless expressly otherwise defined herein.

The terms "proximal" and "distal" are used herein in the common usage sense where they refer respectively to a handle/doctor-end of a device or related object and a tool/patient-end of a device or related object. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof).

Provided are adjustable retractor blades and retractor systems for use in surgery. Also disclosed are methods for using retractor blades in surgery.

In contrast to traditional fixed retractor blades used to retract tissue during surgical applications, the disclosed retractor blades are configured to be adjustable in length and in some cases width, allowing a user to select from (and prepare) a relatively small number of retractor blades for any given surgical procedure. In the surgical theatre, retractor blades are normally used in pairs. A full surgical retractor kit may include 20, 30, or more retractor blades of varying lengths. Using the disclosed adjustable retractor blades, a surgeon may be able to reduce the total number of blades needed to one or two pairs. The adjustability of the disclosed retractor blades and reduced number of required blades allows for a reduction in inventory, less time spent cleaning and sterilizing instruments, and reduced costs, while still providing the necessary size options to operate on patients with varying anatomy.

Adjustable retractor blades may also be referred to herein as adjustable blades, adjustable surgical retractor blades, adjustable surgical retraction blades, adjustable retractors, adjustable retraction blades, adjustable blades for surgical retraction, adjustable retractor blades, extendible retractor blades, and the like. An adjustable retractor blade generally can be configured to allow a user to increase or decrease its longitudinal length (i.e., to make it longer). In this way, an adjustable retractor blade may be configured in one procedure to have a relatively shorter length, and extended (lengthened) to have a longer length in another procedure, thus accomodating greater tissue depths, giving the surgeon greater clearance between the retractor system and surgical site (e.g., for better visibility), or otherwise satisfying user preferences.

The disclosed adjustable retractor blade is particularly useful for surgery of the spine and vertebral column, for example spinal decompression (laminectomy, laminotomy, discectomy), and spinal fusion. The adjustable retractor blade may also be used for retraction of soft tissue in other surgical procedures, including surgeries of the abdomen, chest, or extremities.

The disclosed retractor blades and retractor systems may be manufactured using conventional materials for surgical instruments, including various metals, steels, composites, polymeric materials, and other materials suitable for use in the body and generally capable of being sterilized.

The disclosed retractor blades may also be reusable. Adjustable retractor blades capable of being sterilized and cleaned can be employed in successive surgeries. In some embodiments, a fixed portion and an extendible portion of the disclosed retractor blades are separable for efficient cleaning and sterilization.

In one aspect, an adjustable blade for surgical retraction is thus provided.

An adjustable retractor blade may have a modular design with two or more portions or components, at least one of which can be extended, stacked, expanded, compressed, or otherwise displaced to allow changes in the overall length (or width) of the retractor blade.

Various adjustable retractor blade configurations are thus available to accommodate a range of needed lengths.

In embodiments, the adjustable retractor blade includes a fixed portion and an extendible portion. In some embodiments, the fixed portion includes a proximal end, a distal end, and one or more channels. In some embodiments, the extendible portion is engaged with the one or more channels and longitudinally displaceable therein.

In certain embodiments, the minimum length of an adjustable retractor blade is defined by the length of a fixed portion plus the "overhang" of an extendible portion that extends beyond (i.e., distal to) the distal end of the fixed portion when the extendible portion is contracted. In certain of these embodiments, the maximum length of the adjustable retractor blade is defined by the length of the fixed portion plus the portion of the extendible portion that extends beyond the distal end of the fixed portion when the extendible portion is maximally extended. In such configurations where the fixed portion and extendible portion are roughly equal in length, the maximum length (extended) of the adjustable retractor blade is expected to be about twice the minimum length (contracted) of the adjustable retractor blade. In other configurations, it is envisioned that the length of an extendible portion is significantly greater than or significantly less than the length of a fixed portion.

A single adjustable retractor blade (or matching pair thereof) may be extendible over a range of lengths to cover all required retractor blade lengths. Because retractor blades are normally used in pairs of equal length, it is one object of the disclosure to replace a large set of fixed length retractor blades with a single pair of adjustable length retractor blades. In some embodiments, an adjustable retractor blade is thus adjustable in length in a range from about 30 mm to about 120 mm. In some cases, it may be desirable to provide two or more pairs of adjustable retractor blades to cover a range of sizes. For example, in some embodiments, one adjustable retractor blade is adjustable in length in a range from about 30 mm to about 60 mm, and another adjustable retractor blade is adjustable in length in a range from about 60 mm to about 120 mm. Additional length ranges are also within the scope of the disclosure, including for example: a) 30-50 mm, 50-90 mm, and 80-120 mm; b) 30-60 mm, 50-90 mm, and 80-120 mm; or c) 30-60 mm, 50-90 mm, and 80-150 mm. Thus, a complete (and in some cases overlapping) range of desired lengths may be achieved using either one retractor blade or a small number of adjustable retractor blades. In alternative embodiments, an adjustable retractor blade is adjustable to as low as 20 mm or 25 mm. For example, in certain applications, an adjustable retractor blade may be adjustable in a range from about 25 mm to about 40 mm. Another adjustable retractor blade may be adjustable in a range from about 20 mm to about 35 mm. Other ranges are similarly envisioned and within the scope of the invention.

In embodiments, the adjustable retractor blade includes a means for adjusting the length of the adjustable blade. In embodiments, the adjustable length retractor blade includes a means for adjusting the width of the adjustable blade. In some embodiments, both the length and the width of an adjustable blade are adjustable. Various means for adjusting the length and/or width of the retractor blade exist. For example, screws, ratcheted interfaces (e.g., ratchets and pawls), notches, hinges, grooves, channels, holes (e.g., keyholes), recesses, pins, posts, magnets, and any combinations of these may be used. Depending on the nature of the design used, the means for adjusting the length of the retractor blade may also serve to secure the fixed portion to the extendible portion once a desired length (degree of extension) is reached (i.e., serve as locking means).

In some embodiments, the means for adjusting the length of the retractor blade is a threaded rod or screw.

Accordingly, in embodiments, an adjustable blade for surgical retraction is disclosed, the adjustable blade comprising: a fixed portion having a proximal end, a distal end, and one or more channels; an extendible portion engaged with the one or more channels and longitudinally displaceable therein, the extendible portion extending from the distal end; and means for adjusting the length of the adjustable blade, wherein the means for adjusting comprises a threaded rod or screw engaging the fixed portion with the extendible portion.

In embodiments, a threaded rod or screw is mounted at the proximal end of the fixed portion. In a preferred embodiment, the threaded rod or screw includes a knob at its proximal terminus, the knob configured to control rotation of the threaded rod or screw, such that rotation of the threaded rod or screw displaces an extendible portion longitudinally, with respect to a fixed portion (i.e., lengthens or shortens the retractor overall).

In embodiments, an adjustable retractor blade includes locking means for securing the adjustable blade at a desired length. As noted, these locking means may include screws, ratcheted interfaces (e.g., ratchets and pawls), notches, hinges, grooves, channels, holes (e.g., keyholes), recesses, pins, posts, and combinations of any thereof. Locking means may also include magnets, friction-fittings, springs, and the like. In still other applications, locking means may include the use of alloy wires or springs to modulate a locking mechanism. For example, some medical grade alloy (e.g., nitinol) wires or springs demonstrate conformational changes in response to temperature changes and/or electrical current that may be utilized to control a locking mechanism associated with an adjustable retractor blade.

A threaded rod or screw design provides certain advantages. A threaded rod or screw placed, for example, on the proximal end of a fixed portion of the retractor blade (either on the front face of the fixed portion or on top of the fixed portion) is easily manipulated in theatre by turning a knob attached to the threaded rod or screw using one hand, without the need to disassemble or slide the respective portions of the blade. In this and other embodiments described herein, an adjustable retractor blade is adjustable from a location outside the body of the patient, allowing the surgical field to be maintained without disassembly of the retractor blade or removal of the retractor blade from the retractor frame.

A threaded rod or screw may also generate sufficient resistance to restrict undesired displacement, without the need for a separate locking means on the retractor blade. Accordingly, in some embodiments, a desired length of the adjustable retractor blade is secured by screw tension. This design also allows a user to choose from an essentially continuous range of lengths between a maximum and minimum extension, in contrast to designs with a relatively small number or discrete extension points. Accordingly, the threaded rod or screw design allows great flexibility in operation.

In embodiments, the adjustable retractor blade is configured to attach to a retractor arm. The retractor arm may in turn be attached to a retractor frame. In some embodiments, the fixed portion includes a flange. In certain embodiments, the fixed portion is mounted to a retractor arm at the flange. A flange may be modified to include a slot, screw, pin, threaded opening, or other means for attaching the flange to the retractor arm. Other configurations for mounting the adjustable retractor blade to a retractor arm may also be envisioned, within the scope of the disclosure.

In embodiments, the adjustable blade includes a fixed portion; an extendible portion having a plurality of stackable members; and means for reversibly attaching the plurality of stackable members to each other. In some embodiments, the length of the adjustable blade is adjusted by attaching or detaching members of a plurality of stackable portions to the extendible portion.

Accordingly, in some embodiments, an adjustable blade for surgical retraction is disclosed, the adjustable blade comprising: a fixed portion; an extendible portion comprising a plurality of stackable members, at least one of the plurality of stackable members secured to the fixed portion; and means for reversibly attaching the plurality of stackable members to each other, wherein the length of the adjustable blade is adjusted by attaching or detaching members of the plurality of stackable members to the extendible portion.

In some embodiments, a means for reversibly attaching the plurality of stackable members to each other is selected from magnets, pins/posts and recesses, screws, or a combination of any thereof. Any of these may be positioned at the interface of two stackable portions, to permit firm connection between stackable portions, as discussed further herein. In addition, similar means may be used to attach a plurality of stackable members to a fixed portion.

Retractor blades are frequently modified at their distal end (i.e., tip) in a J-shaped configuration, hook, or bend to facilitate displacement of soft tissue away from the surgical site. The retractor blade tips may also be serrated to more effectively engage soft tissue. Accordingly, in some embodiments, a distal member of the plurality of stackable members includes a curved portion at its distal end, the curved portion having a serrated (i.e., "teeth") edge. It is envisioned that any of various other configurations of adjustable blade described herein may include a similar modification at the distal end (tip) of the extendible portion of the retractor blade.

Accordingly, in some embodiments, a distal member of the plurality of stackable members comprises one of a variety of retractor tips, each retractor tip having a unique serrated or non-serrated (smooth) edge. In this way, the distal member may be interchanged freely to accommodate surgeon preferences and the demands of a given procedure.

In embodiments, the adjustable blade includes a fixed portion having at least one depressable post near its distal end; an extendible portion having one or more channels configured to engage the fixed portion, and a plurality of holes configured to receive the at least one depressable post. In certain embodiments, the length of the adjustable blade is adjusted by slidably displacing the extendible portion until the at least one depressable post engages with at least one of the plurality of holes at a desired length.

Accordingly, in some embodiments, an adjustable blade for surgical retraction is disclosed, the adjustable blade comprising: a fixed portion having a plurality of holes; an extendible portion having at least one post near its distal end, the fixed portion having one or more channels configured to engage the fixed portion, the plurality of holes configured to receive the at least one post, wherein the length of the adjustable blade is adjusted by slidably displacing the extendible portion until the at least one post engages with at least one of the plurality of holes at a desired length.

In some embodiments, the depressable post is spring-loaded. In certain embodiments, at least two depressable posts engage with at least two of the plurality of holes to adjust the length of the adjustable blade. The two depressable posts may be disposed on opposite sides of the fixed portion or in another configuration suited to "locking" the extendible portion with respect to the fixed portion at a desired length. Accordingly, at least one depressable post engaging with at least one of the plurality of holes may provide a suitable locking means for securing the adjustable blade at a desired length.

In one aspect, a surgical retractor system is disclosed.

In embodiments, the surgical retractor system includes a retractor frame, one or more retractor arms, and at least one adjustable retractor blade, the adjustable retractor blade including a fixed portion having a proximal end, a distal end, and one or more channels; an extendible portion engaged with the one or more channels and longitudinally displaceable therein, the extendible portion extending from the distal end; means for adjusting the length of the adjustable blade; and means for mounting the fixed portion to the retractor arm. In some embodiments, a fixed portion includes a flange, the fixed portion mounted to the retractor arm at the flange. In embodiments, the means for adjusting the length of the adjustable blade is a threaded rod or screw engaging the fixed portion with the extendible portion.

In embodiments, the surgical retractor system includes a retractor frame, one or more retractor arms, and at least one adjustable retractor blade, the adjustable retractor blade including a fixed portion having at least one depressable post near its distal end; an extendible portion having one or more channels configured to engage the fixed portion, and a plurality of holes configured to receive the at least one depressable post, wherein the length of the adjustable blade is adjusted by slidably displacing the extendible portion until the at least one depressable post engages with at least one of the plurality of holes at a desired length. In some embodiments, the at least one depressable post is spring-loaded. In some embodiments, at least two depressable posts engage with at least two of the plurality of holes to adjust the length of the adjustable blade.

The disclosure is further illustrated by reference to the drawings provided.

Referring to FIG. 1, a surgical retractor system 100 is provided. Surgical retractor system 100 includes two retractor arms 101 attached to ratcheted frame 102. Ratcheted frame 102 is configured to expand in width to spread open a surgical site. Also shown are two adjustable retractor blades 103. Each adjustable retractor blade 103 includes a flange 106 forming approximately a right angle to the longitudinal axis of each adjustable retractor blade 103. Flange 106 includes slot 107 configured to mount adjustable retractor blade 103 to retractor arm 101. As shown, the end of each retractor arm 101 is fitted within slot 107 and may be secured within slot 107 by friction fitting, screws or bolts (not shown), or other means known generally in the art. Adjustable retractor blade 103 includes fixed portion 104 and extendible portion 105. As shown, each adjustable retractor blade 103 is in a fully extended position.

FIGS. 2 and 3 illustrate an extended and contracted, respectively, adjustable retractor blade 103. As illustrated, fixed portion 104 includes flange 106 and slot 107 in flange 106. Slot 107 is configured to mount fixed portion 104 with a retractor arm (not shown). Extendible portion 105 is engaged with and longitudinally displaceable within channels 110 of fixed portion 104. Threaded rod 108 includes knob 109 mounted at the proximal end of fixed portion 104 and engages fixed portion 104 with extendible portion 105. Rotation of knob 109 causes rotation of threaded rod 108, accordingly causing extended portion 105 to displace longitudinally (extending or contracting, depending on the direction of rotation). Accordingly, the length of adjustable retractor blade 103 may be controlled by operation of knob 109 with threaded rod 108. As shown in FIG. 2, adjustable retractor blade 103 is in a fully extended configuration, achieving its maximal length. FIG. 3 illustrates adjustable retractor blade 103 in its fully contracted configuration, with distance "y" representing the range of extension possible. The distal end of extendible portion 105 further includes curved portion 111, with serrations configured to facilitate capture (engagement with) soft tissue at the surgical site.

Figure 4:
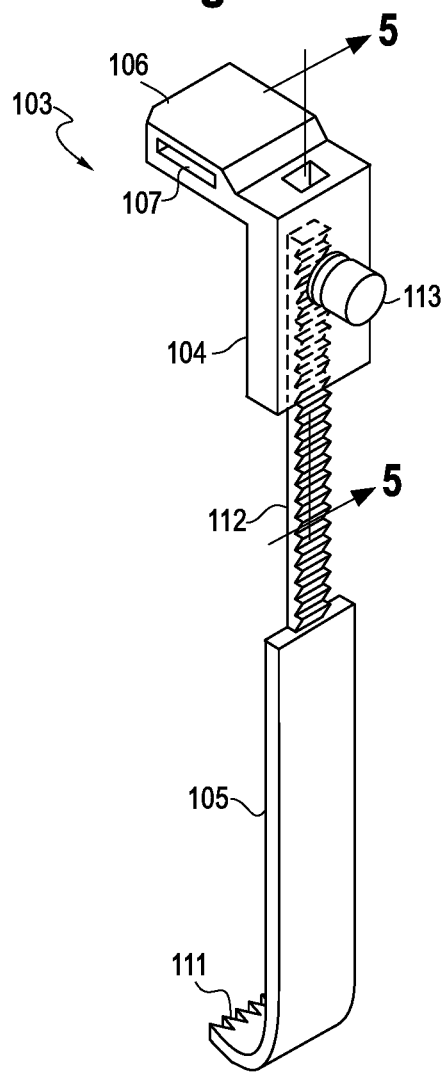
FIG. 4 illustrates a perspective view of an adjustable retractor blade, according to certain embodiments herein.
Figure 5:
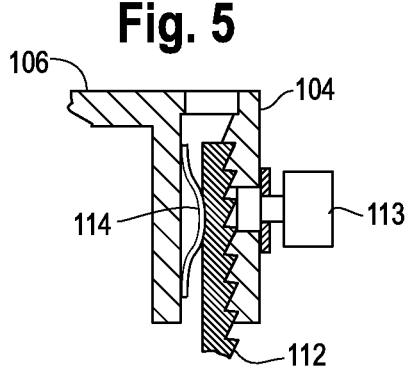
FIG. 5 illustrates a side view of the adjustable retractor blade of FIG. 4, emphasizing one locking means, according to certain embodiments herein.

FIG. 4 illustrates another embodiment of adjustable retractor blade 103. Fixed portion includes flange 106 and slot 107. Extendible portion 105 includes curved portion 111 at its distal end. As shown, fixed portion 104 engages with extendible portion 105 using ratchet 112, with fixed portion 104 and/or extendible portion 105 configured to include one or more channels for receiving ratchet 112. In the side view of FIG. 5, ratchet 112 is illustrated within such a channel in fixed portion 104, with the teeth of ratchet 112 engaged with corresponding teeth inside the channel within fixed portion 104. In this way, ratchet 112 provides locking means for securing the adjustable blade at a desired length. Bolt 113 is depressable against ratchet 112 to disengage the teeth of ratchet 112 and allow extendible portion 105 to be extended or contracted longitudinally through manual operation of the user. Spring 114 provides a bias force against ratchet 112 to reengage the teeth of ratchet 112 with the corresponding teeth inside the channel once a desired length for adjustable retractor blade 103 is achieved.

Figure 6:
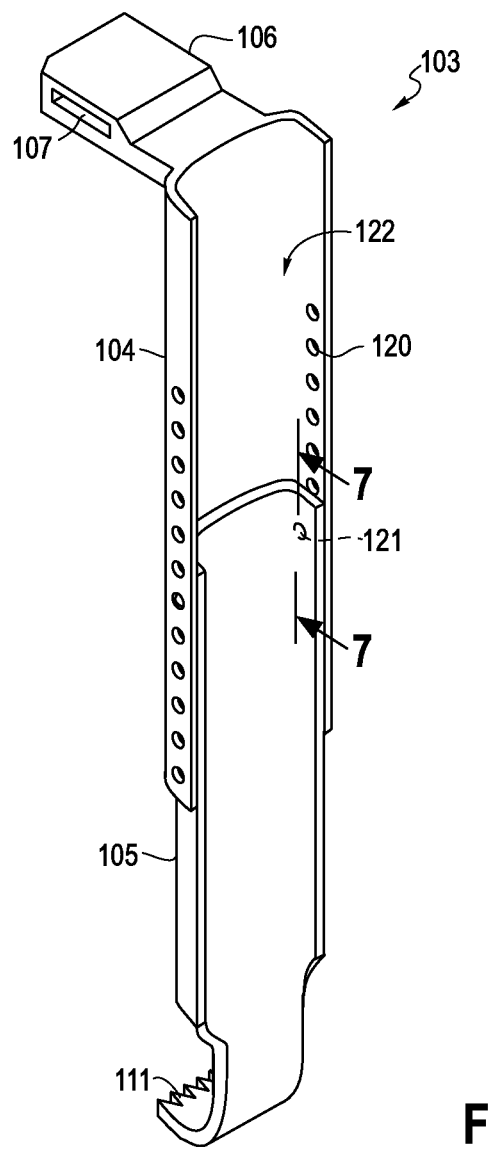
FIG. 6 illustrates a perspective view of an adjustable retractor blade, according to certain embodiments herein.
Figure 7:
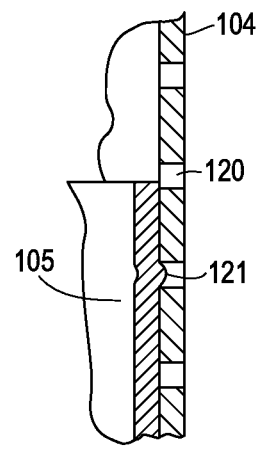
FIG. 7 illustrates a frontal view of the adjustable retractor blade of FIG. 6, emphasizing one locking means, according to certain embodiments herein.

FIG. 6 illustrates another embodiment of adjustable retractor blade 103. Fixed portion includes flange 106 and slot 107. Extendible portion 105 includes curved portion 111 at its distal end. As shown, fixed portion 104 includes channel 122, which engages with and allows extendible portion 105 to slide therewithin, and a plurality of holes 120 along a majority of the length of the lateral edges of channel 122. The number and spacing of holes 120 determines the range of lengths that may be selected for adjustable retractor blade 103. Extendible portion 105 includes posts 121 along the lateral inside edge at its proximal end. While FIG. 6 shows one post 121, in a preferred embodiment, a corresponding post 121 is also present on the opposite inside edge of extendible portion 105 (not shown). FIG. 7 illustrates a close frontal view of adjustable retractor blade 103 from FIG. 6, emphasizing engagement of post 121 with hole 120. In the illustrated embodiments, the length of the adjustable retractor blade 103 is adjusted by slidably displacing extendible portion 105 until one or more posts 121 engage with one or more holes 120, as shown. Engagement of post 121 with hole 120 thus provides both a means for adjusting the length of adjustable retractor blade 103 and a locking means for securing adjustable retractor blade 103 at a desired length. In some embodiments, a friction fit is achieved by the engagement of post 121 with hole 120 and no additional mechanism may be required. In other embodiments, post 121 is spring-loaded and depressable, allowing a deeper engagement of post 121 with hole 120 and potentially a more secure locking means once the desired length is achieved.

FIGS. 8-10 illustrate another embodiment of adjustable retractor blade 103. As shown, fixed portion 104 includes ratchet 131 and forms channel 122 for engaging extendible portion 105. Fixed portion 104 is configured to mount to retractor arm 101 (not shown) using means generally known in the art. Ratchet 131 of fixed portion 104 is configured as a depressable/releasable tab. Ratchet 131 may be spring-loaded. A plurality of notches 130 on a lateral edge of extendible portion 105 is configured to engage with ratchet 131. In the embodiment of FIGS. 8 and 9, notches 130 are present only on one edge of extendible portion 105. However, in some embodiments, notches 130 and ratchet 131 are present on both edges of extendible portion 105 and fixed portion 104, respectively (i.e., on both the left and right sides of FIG. 9). FIG. 10 illustrates a top view of an isolated notch 130 in certain embodiments. Other shapes and configurations for notch 130 and ratchet 131 may also be envisioned. In operation, ratchet 131 engages with notch 130 as shown in FIGS. 9 and 10. Depression of ratchet 131 disengages ratchet 131 from notch 130 and allows extendible portion 105 to slide longitudinally with respect to fixed portion 104 until a desired length for adjustable retractor blade 103 is reached, at which point a user may release ratchet 131 and allow it to reengage with a (different) notch 130 at a different position. The design of notch 130, as shown in more detail in FIG. 10, allows ratchet 131 to engage notch 130 from either a top or bottom approach. Notch 130 and ratchet 131 thus provide a means for adjusting the length of adjustable retractor blade 103, and a locking means for securing the adjustable blade at a desired length, when ratchet 131 is in a "resting" (non-depressed) position. In some embodiments, notches 130 can be labelled to indicate the length corresponding to each such notch 130, for user convenience.

Figure 11:
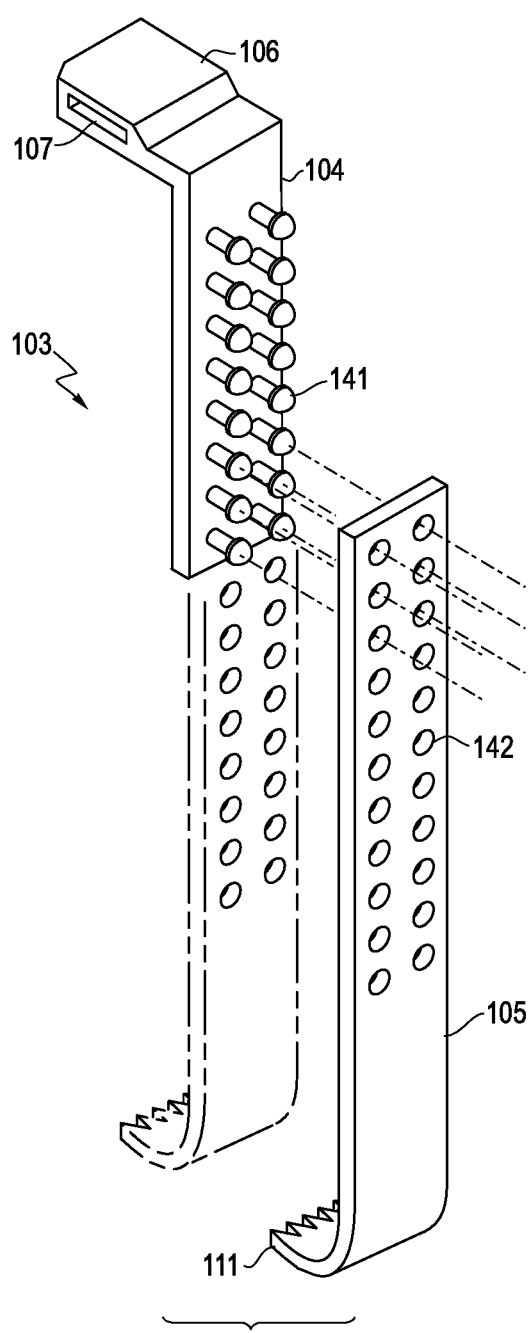
FIG. 11 illustrates a perspective view of an adjustable retractor blade, according to certain embodiments herein.
Figure 12:
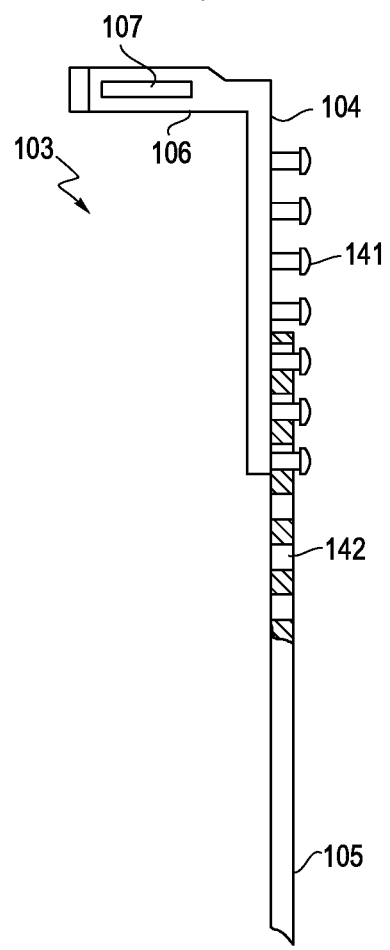
FIG. 12 illustrates a side view of an adjustable retractor blade emphasizing a possible locking mechanism, according to certain embodiments herein.

FIGS. 11 and 12 illustrate another embodiment of adjustable retractor blade 103. Fixed portion includes flange 106 and slot 107. Extendible portion 105 includes curved portion 111 at its distal end with serrations for capturing soft tissue. As shown, fixed portion 104 further includes two rows of pins 141 with rounded or flared heads. Extendible portion 105 includes two corresponding rows of holes configured to receive pins 141. FIGS. 11 and 12 thus illustrate one embodiment of what may be described as a "snap-fit" configuration for adjustable retractor blade 103. Other configurations are also encompassed, including configurations with one, three, or more rows of pins 141 and corresponding holes 142 are present, configurations in which pins 141 and corresponding holes 142 are offset in the longitudinal axis, rather than aligned as shown in FIG. 11, and configurations in which pins 141 are present on extendible portion 105 and holes 142 are present on fixed portion 104. In operation, a user may disengage extendible portion 105 from fixed portion 104 by pulling extendible portion 105 away from fixed portion 104 as illustrated in FIG. 11. The user then may manually displace extendible portion 105 in a longitudinal axis (up or down) until a desired length is obtained for adjustable retractor blade 103, at which point the user may engage extendible portion 105 with fixed portion 104 by aligning pins 141 at the desired position with holes 142 and applying force to "snap" the two pieces together. FIG. 12 illustrates a side view of adjustable retractor blade 103 in an engaged configuration. Engagement of fixed portion 104 and extendible portion 105 in this snap-fit configuration thus serves as a means for adjusting the length of adjustable retractor blade 103, a stop means for preventing disengagement of the fixed portion and the extendible portion, and a locking means for securing the adjustable blade at a desired length.

Figure 13:
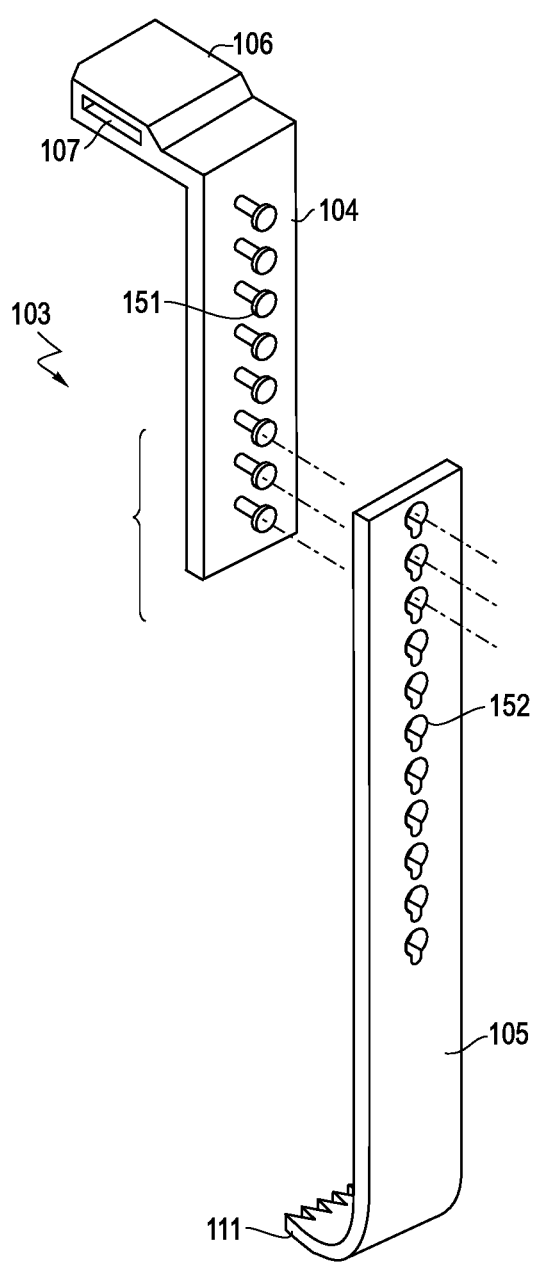
FIG. 13 illustrates a perspective view of an adjustable retractor blade, according to certain embodiments herein.
Figure 14:
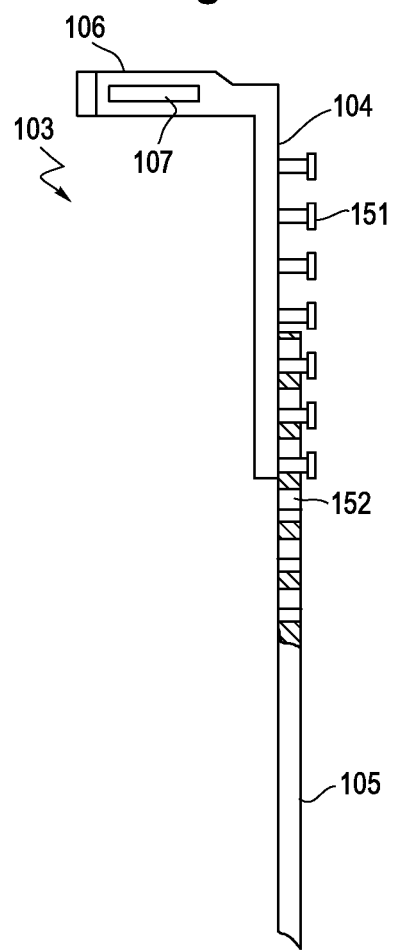
FIG. 14 illustrates a side view of an adjustable retractor blade emphasizing a possible locking mechanism, according to certain embodiments herein.

FIGS. 13 and 14 illustrate another embodiment of adjustable retractor blade 103. Fixed portion 104 includes flange 106 and slot 107. Extendible portion 105 includes curved portion 111 at its distal end with serrations for capturing soft tissue. As shown, fixed portion 104 further includes one rows of pegs 151 with widened heads disposed along a central longitudinal axis of fixed portion. Extendible portion 105 includes a corresponding row of key holes 152 configured to receive pegs 151. As shown in FIG. 13, key holes 152 narrow at one end (here shown as the distal end of each such key hole 152). FIGS. 13 and 14 thus illustrate one embodiment of what may be described as a "key hole lock" configuration for adjustable retractor blade 103. Other configurations are also encompassed, including configurations with two, three, or more rows of pegs 151 and key holes 152, configurations in which two or more rows of pegs 151 and key holes 152 are offset in the longitudinal axis, configurations in which the narrow ends of key holes 152 are on the proximal end of key holes 152, and configurations in which pegs 151 are present on extendible portion 105 and key holes 152 are present on fixed portion 104. In operation, a user may disengage extendible portion 105 from fixed portion 104 by pulling extendible portion 105 away from fixed portion 104 as illustrated in FIG. 13. The user then may manually displace extendible portion 105 in a longitudinal axis (i.e., up or down) until a desired length is obtained for adjustable retractor blade 103, at which point the user may engage extendible portion 105 with fixed portion 104 by aligning and inserting pegs 151 into the wide openings of corresponding key holes 152 at the desired position and sliding extendible portion 105 "up" slightly with respect to fixed portion 104 to lock pegs 151 in key holes 152. Alternatively, the user may engage a different extendible portion 105 having a differing curved portion 111 with either a distinct serrated edge or a non-serrated edge, to accommodate surgeon preferences and the demands of a given procedure.

FIG. 14 illustrates a side view of adjustable retractor blade 103 in an engaged configuration, as described. Engagement of fixed portion 104 and extendible portion 105 in this "key hole lock" configuration thus serves as a means for adjusting the length of adjustable retractor blade 103, a stop means for preventing disengagement of the fixed portion and the extendible portion, and a locking means for securing the adjustable blade at a desired length.

FIGS. 15 and 16 illustrate another embodiment of adjustable retractor blade 103. Adjustable retractor blade 103 includes fixed portion 104, having flange 106 and slot 107 for attachment of fixed portion 104 with retractor arm 101 (not shown). Unlike some other embodiments described herein, extendible portion 105 is comprised of a plurality of stackable members 161. At least one of the plurality of stackable members 161 is secured to fixed portion 104. As shown, the body of the proximal stackable member 161 passes through an opening in fixed portion 104 and is secured by, for example, a friction fitting. A user accordingly increases or decreases the length of adjustable retractor blade 103 by adding or removing stackable members 161 from extendible portion 105. As shown, a proximal stackable member 161 is attached to cap 160. Cap 160 includes an enlarged (flared) portion that is larger than an opening provided in fixed portion 104 through which the proximal stackable member 161 passes. Cap 160 thus may serve as a stop to prevent stackable members 161 of extendible portion 105 from sliding out of or fully disengaging from fixed portion 104. Each of stackable members 161 includes a means for reversibly attaching the plurality of stackable members 161 to each other. As shown in FIG. 15, each stackable member 161 includes pins 164 on its proximal edge which fit into recesses 163 on the distal edge of the stackable member above it, to form coupling 162. Distal member 166 of the plurality of stackable members 161 includes curved portion 111 at its distal end, the curved portion 111 having a serrated edge. In another embodiment using this stackable member configuration (illustrated in FIG. 16), magnets 165 at the distal edge and proximal edge of adjacent stackable members 161 are used to form coupling 162. Stackable members 161 may be of the same or different lengths, allowing for a substantial variation in possible lengths of the overall adjustable retractor blade 103.

While distal member 166 as shown includes curved portion 111 having a serrated edge, a variety of alternative distal members 166 may be utilized to accommodate surgeon preference and the needs of a given procedure. In some embodiments, distal member 166 is shorter or longer. In some embodiments, curved portion 111 has a variety of serrated patterns. In some embodiments, curved portion 111 has a non-serrated edge. In some embodiments, the curvature of curved portion 111 may be steeper or more shallow.

FIG. 17 illustrates another embodiment of adjustable retractor blade 103. As shown, adjustable retractor blade 103 includes proximal hinged portion 170, body 171, and distal hinged portion 172, connected via hinges 173. Hinged portions 170 and 172 may be opened and closed by rotation about hinges 173. In some embodiments, hinges 173 may incorporate a stop preventing hinged portions 170 and 172 from opening beyond the plane of body 171. Alternatively, or in addition, hinges 173 may incorporate a ratchet and release mechanism (not shown) such that hinged portions 170 and 172 may be freely opened up to the plane of body 171, but require engagement of a release before they can be closed. Arrows in FIG. 17 indicate the direction of opening and closing. As shown, hinged portion 172 includes curved portion 174 at its distal end. As shown, adjustable retractor blade 103 may be mounted to retractor frame 100 (not shown) via retractor arm 101 (not shown) using slots or any of a variety of conventional means attached at hinged portion 170 or body 171. It is also envisioned that additional hinges and hinged portions may be included within the configuration. For example, hinged portion 172 may include an internal hinge subdividing hinged portion 172 and allowing further refinement in length of adjustable retractor blade 103.

FIGS. 18 and 19 illustrate another embodiment of adjustable retractor blade 103. Fixed portion 104 includes flange 106 and slot 107. Extendible portion 105 includes two holes 180 and vertical slot 182 disposed along a central longitudinal axis of extendible portion 105. Fixed portion 104 further includes spring-loaded pin 183 and two capped pins 181. Capped pins 181 are configured to engage with and be slidably displaceable within vertical slot 182. Spring-loaded pin 183 is configured to engage with and lock into holes 180, as shown in FIG. 19. In operation, a user longitudinally displaces (slides) extendible portion 105 with respect to fixed portion 104 until spring-loaded pin engages with hole 180 at a desired length for adjustable retractor blade 103. Capped pins 181 prevents disengagement of fixed portion 104 and extendible portion 105, while vertical slot 182 maintains alignment of fixed portion 104 and extendible portion 105. As shown, extendible portion includes only two holes 180. However, additional configurations utilizing three, four, or more holes 180 may readily be envisioned, facilitating a wide range of length options.

Figure 20:
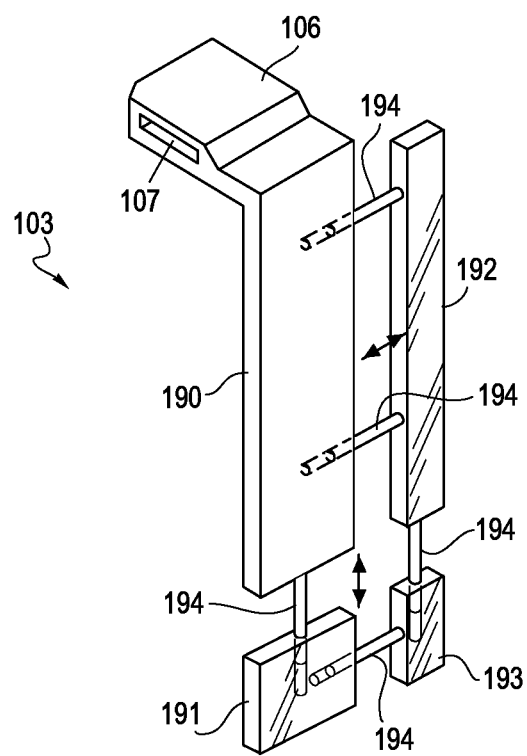
FIG. 20 illustrates a perspective view of an adjustable retractor blade, according to certain embodiments herein.

FIG. 20 illustrates another embodiment of adjustable retractor blade 103. Proximal left portion 190 includes flange 106 and slot 107. Unlike some other configurations described herein, the embodiment of FIG. 20 provides a further mechanism for adjusting the width and length of adjustable retractor blade 103. As shown, proximal left portion 190 attaches to distal left portion 191 and proximal right portion 192. Proximal right portion 192 is in turn attached to distal right portion 193. Each of proximal left portion 190, distal left portion 191, proximal right portion 192, and distal right portion 193 are connected to each other using connectors 194, which may be pins, dowels, screws, bolts, or any suitable connectors allowing the respective connected portions to be pulled apart and put closer together repeatedly. As shown, a horizontal set of connectors 194 may thus be used to expand or contract the width of adjustable retractor blade 103 and a vertical set of connectors 194 may be used to expand or contract the length of adjustable retractor blade 103, as desired. In some embodiments, each of proximal left portion 190, distal left portion 191, proximal right portion 192, and proximal right portion 192 may be formed of a clear material and one or more of these may further include a lighting element, to improve visibility and ease of adjustment. As shown, distal left portion 191 is configured as forming a vertical extension of proximal left portion 190. However, in other configurations, each of proximal left portion 190, distal left portion 191, proximal right portion 192, and distal right portion 193 may be distinct structures, one of which is connected to proximal left portion 190 using means as described herein. In addition, while the configuration of FIG. 20 includes a total of four adjustable portions, it is also envisioned that additional portions may be added to adjustable retractor blade 103 within the scope of the invention, for example retractor blade 103 may include a middle proximal portion and middle distal portion in addition to the portions described hereinabove. Further, distal left portion 191 and/or distal right portion 193 may include a curved portion at their distal end, the curved portion either serrated or non-serrated for engaging with soft tissue.

The foregoing drawings illustrate certain embodiments of adjustable retractor blade 103 and retractor system 100. It is understood that features described as being present on fixed portion 104 may instead be present on extendible portion 105 of adjustable retractor blade 103, and features described as being present on extendible portion 105 may instead be present on fixed portion 104, without deviating from the scope and spirit of the invention.

In one aspect, methods are disclosed for adjusting the length of a retractor blade.

In one embodiment, a method includes determining a desired length of a surgical retractor blade, the surgical retractor blade having a fixed portion having a proximal end, a distal end, and one or more channels, an extendible portion engaged with the one or more channels and longitudinally displaceable therein, the extendible portion extending from the distal end, and means for adjusting the length of the adjustable blade, wherein the means for adjusting comprises a threaded rod or screw engaging the fixed portion with the extendible portion; engaging the fixed portion with the extendible portion; and rotating the threaded rod or screw until the desired length is achieved.

In one embodiment, a method includes determining a desired length of a surgical retractor blade, the retractor blade comprising a fixed portion, an extendible portion comprising a plurality of stackable members, at least one of the plurality of stackable members secured to the fixed portion, and means for reversibly attaching the plurality of stackable members to each other; and attaching or detaching members of the plurality of stacking members to the extendible portion until a desired length is achieved.

In one embodiment, a method includes determining a desired length of a surgical retractor blade, the surgical retractor blade having a fixed portion having a plurality of holes, an extendible portion having at least one post near its distal end, the fixed portion having one or more channels configured to engage the fixed portion, the plurality of holes configured to receive the at least one post; engaging the fixed portion with the extendible portion; and slidably displacing the extendible portion until the at least one post engages with at least one of the plurality of holes at a desired length.

Methods for adjusting the length of a retractor blade also include any of the other embodiments for adjustable retractor blades disclosed herein, and any embodiments that are reasonably within the scope of the disclosure.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. An adjustable blade assembly for surgical retraction, the adjustable blade assembly comprising:
    a fixed portion having a proximal end, a distal end, and one or more channels;
    an extendible blade engaged with the one or more channels and longitudinally displaceable therein, the extendible blade extending from the distal end; and
    a threaded rod or screw threadably engaged with the fixed portion such that rotation of the threaded rod or screw retracts or extends the threaded rod or screw and the extendible blade relative to the fixed portion;
    wherein the threaded rod or screw translates with the extendible blade as the threaded rod or screw rotates, the extendible blade having a proximal end located in the one or more channels that is connected to a terminal end of the threaded rod or screw.

2. The adjustable blade assembly of claim 1, wherein the extendible blade extends away from a terminal end of the threaded rod or screw.

3. The adjustable blade assembly of claim 1, wherein rotation of the threaded rod or screw displaces the extendible blade longitudinally.

4. The adjustable blade assembly of claim 1, wherein the desired length of the adjustable blade assembly is secured by screw tension.

5. The adjustable blade assembly of claim 1, wherein the extendible blade is adjustable in length relative to the fixed portion in a range from about 30 mm to about 120 mm.

6. The adjustable blade assembly of claim 1, further comprising a stop configured to inhibit disengagement of the fixed portion and the extendible blade.

7. The adjustable blade assembly of claim 1, further comprising a lock configured to secure the extendible blade at a desired length.

8. The adjustable blade assembly of claim 1, wherein the fixed portion further comprises a flange.

9. The adjustable blade assembly of claim 8, wherein the fixed portion is configured to mount to a retractor arm at the flange.

10. An adjustable blade assembly for surgical retraction, the adjustable blade comprising:
    a fixed portion having a proximal end, a distal end, and one or more channels;
    an extendible blade engaged with the one or more channels and longitudinally displaceable therein, the extendible blade extending from the distal end; and
    a threaded rod or screw threadably engaged with the fixed portion, the threaded rod or screw having a distal portion and a proximal portion, wherein the extendible blade has a proximal end located in the one or more channels and extends from a terminal end of the distal portion of the threaded rod or screw;
    wherein the threaded rod or screw translates with the extendible blade as the threaded rod or screw rotates.

11. The adjustable blade assembly of claim 10, wherein rotation of the threaded rod or screw displaces the extendible blade linearly relative to the fixed portion.

12. The adjustable blade assembly of claim 10, wherein the extendible blade is adjustable in length relative to the fixed portion in a range from about 30 mm to about 120 mm.

13. The adjustable blade assembly of claim 10, further comprising a stop configured to inhibit disengagement of the fixed portion and the extendible blade.

14. The adjustable blade assembly of claim 10, further comprising a lock configured to secure the blade blade at a desired length.

15. The adjustable blade assembly of claim 10, wherein the fixed portion further comprises a flange extending outward in a direction substantially perpendicular to a longitudinal direction.

16. The adjustable blade assembly of claim 15, wherein the fixed portion is configured to mount to a retractor arm at the flange.

17. The adjustable blade assembly of claim 10, wherein the extendible blade and the threaded rod or screw move longitudinally together between extended and retracted positions.

18. A method of adjusting an adjustable retractor blade assembly, the method comprising:
   rotating a threaded rod or screw that is threadably connected to a fixed portion at a connecting location, the fixed portion having a proximal end, a distal end, and one or more channels;
   adjusting a length of an extendible blade relative to the distal end of the fixed portion as the threaded rod or screw rotates, the extendible blade has a proximal end located in the one or more channels and extending from a distal end of the threaded rod or screw engaged with the one or more channels and longitudinally displaceable therein; and
   adjusting a length of the threaded rod or screw extending proximally from the connecting location as the threaded rod or screw rotates;
   wherein the threaded rod or screw translates with the extendible blade as the threaded rod or screw rotates.

19. The method of claim 18 comprising moving the threaded rod or screw linearly with the extendible blade as the threaded rod or screw rotates.

20. The method of claim 19, wherein the extendible blade is adjustable in length relative to the fixed portion in a range from about 30 mm to about 120 mm.

* * * * *